(12) United States Patent
Toubia et al.

(10) Patent No.: US 8,083,733 B2
(45) Date of Patent: Dec. 27, 2011

(54) CRYOSURGICAL INSTRUMENT WITH ENHANCED HEAT EXCHANGE

(75) Inventors: Didier Toubia, Raanana (IL); Alexander Levin, Binyamina (IL); Miron Kaganovich, Haifa (IL)

(73) Assignee: IceCure Medical Ltd., Caesarea (IL)

( * ) Notice: Subject to any disclaimer, the term of this patent is extended or adjusted under 35 U.S.C. 154(b) by 0 days.

(21) Appl. No.: 12/988,233

(22) PCT Filed: Apr. 13, 2009

(86) PCT No.: PCT/IB2009/051532
§ 371 (c)(1),
(2), (4) Date: May 18, 2011

(87) PCT Pub. No.: WO2009/128014
PCT Pub. Date: Oct. 22, 2009

(65) Prior Publication Data
US 2011/0224662 A1     Sep. 15, 2011

Related U.S. Application Data

(60) Provisional application No. 61/045,372, filed on Apr. 16, 2008.

(51) Int. Cl.
*A61B 18/02* (2006.01)
(52) U.S. Cl. .......................................... 606/23; 606/20
(58) Field of Classification Search ............... 606/20–26
See application file for complete search history.

(56) References Cited

U.S. PATENT DOCUMENTS

| 3,234,746 A | 2/1966 | Smith |
| 3,358,472 A | 12/1967 | Kipling |
| 3,664,344 A | 5/1972 | Bryne |
| 3,699,775 A | 10/1972 | Cowans |
| 3,712,306 A | 1/1973 | Bryne |
| 3,736,936 A | 6/1973 | Basiulis |
| 3,800,552 A | 4/1974 | Sollami |
| 3,862,630 A | 1/1975 | Balamuth |
| 3,882,849 A | 5/1975 | Jamshidi |
| 3,938,505 A | 2/1976 | Jamshidi |
| 3,971,383 A | 7/1976 | Van Gerven |
| 4,082,096 A | 4/1978 | Benson |

(Continued)

FOREIGN PATENT DOCUMENTS
CA        2437079       6/2004
(Continued)

OTHER PUBLICATIONS

Verkin Bi et al, "Low temperatures in stomatology", Naukova Dumka, Kiev, 1990, pp. 62-63.

(Continued)

*Primary Examiner* — Michael Peffley
*Assistant Examiner* — Daniel Fowler
(74) *Attorney, Agent, or Firm* — The Law Office of Michael E. Kondoudis (57) ABSTRACT

A cryosurgical instrument features a cryogen in liquid or liquid-gaseous (mist) form being supplied by a feeding lumen into the internal space of a cryotip at the distal end of the cryosurgical instrument. The distal section of the feeding lumen is helically coiled, so that an outer diameter of the helically coiled distal section fits an inner diameter of a cylindrical envelope of said cryotip, and said helically coiled distal section and said cylindrical envelope are in thermal contact.

6 Claims, 5 Drawing Sheets

U.S. PATENT DOCUMENTS

| | | |
|---|---|---|
| 4,091,634 A | 5/1978 | Shepherd |
| 4,127,903 A | 12/1978 | Schachar |
| 4,200,104 A | 4/1980 | Harris |
| 4,211,231 A | 7/1980 | Rzasa |
| 4,279,626 A | 7/1981 | Buchmuller |
| 4,306,568 A | 12/1981 | Torre |
| 4,313,306 A | 2/1982 | Torre |
| 4,367,744 A | 1/1983 | Sole |
| 4,428,748 A | 1/1984 | Peyman |
| 4,463,458 A | 8/1984 | Seidner |
| 4,481,948 A | 11/1984 | Sole |
| 4,487,253 A | 12/1984 | Malek |
| 4,552,208 A | 11/1985 | Sorensen |
| 4,570,626 A | 2/1986 | Norris |
| 4,573,525 A | 3/1986 | Boyd |
| 4,611,654 A | 9/1986 | Buchsel |
| 4,617,018 A | 10/1986 | Nishi |
| 4,676,225 A | 6/1987 | Bartera |
| 4,726,194 A | 2/1988 | Mackay |
| 4,765,396 A | 8/1988 | Seidenberg |
| 4,770,171 A | 9/1988 | Sweren |
| 4,802,475 A | 2/1989 | Weshahy |
| 4,831,856 A | 5/1989 | Gano |
| 4,946,460 A | 8/1990 | Merry |
| 5,026,387 A | 6/1991 | Thomas |
| 5,047,043 A | 9/1991 | Kubota |
| 5,108,390 A | 4/1992 | Potocky |
| 5,147,355 A | 9/1992 | Friedman |
| 5,188,102 A | 2/1993 | Idemoto |
| 5,214,925 A | 6/1993 | Hoy |
| 5,222,937 A | 6/1993 | Kagawa |
| 5,224,943 A | 7/1993 | Goddard |
| 5,243,826 A | 9/1993 | Longsworth |
| 5,254,082 A | 10/1993 | Takase |
| 5,254,116 A | 10/1993 | Baust |
| 5,261,923 A | 11/1993 | Soares |
| 5,263,957 A | 11/1993 | Davison |
| 5,264,116 A | 11/1993 | Apelian |
| 5,275,595 A | 1/1994 | Dobak |
| 5,281,215 A | 1/1994 | Milder |
| 5,295,484 A | 3/1994 | Marcus |
| 5,324,286 A | 6/1994 | Fowle |
| 5,330,745 A | 7/1994 | Mcdow |
| 5,334,181 A | 8/1994 | Rubinsky |
| 5,342,380 A | 8/1994 | Hood |
| 5,361,591 A | 11/1994 | Caldwell |
| 5,391,144 A | 2/1995 | Sakurai |
| 5,411,374 A | 5/1995 | Gram |
| 5,417,073 A | 5/1995 | James |
| 5,423,807 A | 6/1995 | Milder |
| 5,429,138 A | 7/1995 | Jamshidi |
| 5,438,837 A | 8/1995 | Caldwell |
| 5,441,512 A | 8/1995 | Muller |
| 5,445,462 A | 8/1995 | Johnson |
| 5,452,582 A | 9/1995 | Longsworth |
| 5,488,831 A | 2/1996 | Griswold |
| 5,516,505 A | 5/1996 | Mcdow |
| 5,520,682 A | 5/1996 | Baust |
| 5,526,821 A | 6/1996 | Jamshidi |
| 5,547,473 A | 8/1996 | Peyman |
| 5,573,532 A | 11/1996 | Chang |
| 5,600,143 A | 2/1997 | Roberts |
| 5,647,868 A | 7/1997 | Chinn |
| 5,654,279 A | 8/1997 | Rubinsky |
| 5,658,276 A | 8/1997 | Griswold |
| 5,674,218 A | 10/1997 | Rubinsky |
| 5,683,592 A | 11/1997 | Bartholomew |
| 5,687,776 A | 11/1997 | Forgash |
| 5,716,353 A | 2/1998 | Matsuura |
| 5,720,743 A | 2/1998 | Bischof |
| 5,728,130 A | 3/1998 | Ishikawa |
| 5,735,845 A | 4/1998 | Zupkas |
| 5,771,946 A | 6/1998 | Kooy |
| 5,787,940 A | 8/1998 | Bonn |
| 5,800,448 A | 9/1998 | Banko |
| 5,800,487 A | 9/1998 | Mikus |
| 5,814,040 A | 9/1998 | Nelson |
| 5,868,673 A | 2/1999 | Vesely |
| 5,885,276 A | 3/1999 | Ammar |
| 5,899,897 A | 5/1999 | Rabin |
| 5,906,612 A | 5/1999 | Chinn |
| 5,906,628 A | 5/1999 | Miyawaki |
| 5,910,104 A | 6/1999 | Dobak |
| 5,921,982 A | 7/1999 | Lesh |
| 5,976,092 A | 11/1999 | Chinn |
| 5,976,505 A | 11/1999 | Henderson |
| 5,992,158 A | 11/1999 | Goddard |
| 6,012,453 A | 1/2000 | Tsais |
| 6,024,750 A | 2/2000 | Mastri |
| 6,027,499 A | 2/2000 | Johnston |
| 6,032,068 A | 2/2000 | Daniel |
| 6,032,675 A | 3/2000 | Rubinsky |
| 6,035,657 A | 3/2000 | Dobak |
| 6,036,667 A | 3/2000 | Manna |
| 6,039,730 A | 3/2000 | Rabin |
| 6,041,787 A | 3/2000 | Rubinsky |
| 6,042,342 A | 3/2000 | Orian |
| 6,053,906 A | 4/2000 | Honda |
| 6,059,820 A | 5/2000 | Baronov |
| 6,063,098 A | 5/2000 | Houser |
| 6,095,149 A | 8/2000 | Sharkey |
| 6,142,991 A | 11/2000 | Schatzberger |
| 6,152,894 A | 11/2000 | Kubler |
| 6,182,666 B1 | 2/2001 | Dobak |
| 6,200,308 B1 | 3/2001 | Pope |
| 6,206,832 B1 | 3/2001 | Downey |
| 6,212,904 B1 | 4/2001 | Arkharov |
| 6,216,029 B1 | 4/2001 | Paltieli |
| 6,235,018 B1 | 5/2001 | LePivert |
| 6,237,355 B1 | 5/2001 | Li |
| 6,251,105 B1 | 6/2001 | Mikus |
| 6,270,494 B1 | 8/2001 | Kovalcheck |
| 6,280,407 B1 | 8/2001 | Manna |
| 6,354,088 B1 | 3/2002 | Emmer |
| 6,355,033 B1 | 3/2002 | Moorman |
| 6,358,264 B2 | 3/2002 | Banko |
| 6,379,348 B1 | 4/2002 | Onik |
| 6,383,180 B1 | 5/2002 | Lalonde |
| 6,383,181 B1 | 5/2002 | Johnston |
| 6,411,852 B1 | 6/2002 | Danek |
| 6,413,263 B1 | 7/2002 | Lobdill |
| 6,423,009 B1 | 7/2002 | Downey |
| 6,432,102 B2 | 8/2002 | Joye |
| 6,457,212 B1 | 10/2002 | Craig |
| 6,468,268 B1 | 10/2002 | Abboud |
| 6,468,269 B1 | 10/2002 | Korpan |
| 6,471,217 B1 | 10/2002 | Hayfield |
| 6,482,178 B1 | 11/2002 | Andrews |
| 6,497,714 B1 | 12/2002 | Ishikawa |
| 6,500,109 B2 | 12/2002 | Tokita |
| 6,503,246 B1 | 1/2003 | Har-Shai |
| 6,508,814 B2 | 1/2003 | Tortal |
| 6,513,336 B2 | 2/2003 | Zurecki |
| 6,547,784 B1 | 4/2003 | Thompson |
| 6,551,309 B1 | 4/2003 | LePivert |
| 6,562,030 B1 | 5/2003 | Abboud |
| 6,565,556 B1 | 5/2003 | Korpan |
| 6,581,390 B2 | 6/2003 | Emmer |
| 6,582,426 B2 | 6/2003 | Moorman |
| 6,631,615 B2 | 10/2003 | Drube |
| 6,640,556 B2 | 11/2003 | Ursan |
| 6,659,730 B2 | 12/2003 | Gram |
| 6,659,956 B2 | 12/2003 | Barzell |
| 6,672,095 B1 | 1/2004 | Luo |
| 6,678,621 B2 | 1/2004 | Wiener |
| 6,682,525 B2 | 1/2004 | Lalonde |
| 6,698,423 B1 | 3/2004 | Honkonen |
| 6,702,761 B1 | 3/2004 | Damadian |
| 6,761,715 B2 | 7/2004 | Carroll |
| 6,765,333 B1 | 7/2004 | Mariaucue |
| 6,768,917 B1 | 7/2004 | Van Vaals |
| 6,772,766 B2 | 8/2004 | Gallo |
| 6,786,902 B1 | 9/2004 | Rabin |
| 6,824,543 B2 | 11/2004 | Lentz |
| 6,852,706 B1 | 2/2005 | Heber-Katz |
| 6,858,025 B2 | 2/2005 | Maurice |
| 6,869,439 B2 | 3/2005 | White |

| | | |
|---|---|---|
| 6,889,695 B2 | 5/2005 | Pankratov |
| 6,898,940 B2 | 5/2005 | Gram |
| 6,908,472 B2 | 6/2005 | Wiener |
| 6,910,510 B2 | 6/2005 | Gale |
| 6,913,604 B2 | 7/2005 | Mihalik |
| 6,929,639 B2 * | 8/2005 | Lafontaine .................. 606/20 |
| 6,932,771 B2 | 8/2005 | Whitmore |
| 6,936,045 B2 | 8/2005 | Yu |
| 6,942,659 B2 | 9/2005 | Lehmann |
| 6,951,569 B2 | 10/2005 | Nohilly |
| 6,954,977 B2 | 10/2005 | Maguire |
| 6,995,493 B2 | 2/2006 | Isoda |
| 7,001,378 B2 | 2/2006 | Yon |
| 7,025,762 B2 | 4/2006 | Johnston |
| 7,025,767 B2 | 4/2006 | Schaefer |
| 7,071,690 B2 | 7/2006 | Butts |
| 7,081,111 B2 | 7/2006 | Svaasand |
| 7,101,367 B2 | 9/2006 | Xiao |
| 7,128,739 B2 | 10/2006 | Prakash |
| 7,144,228 B2 | 12/2006 | Emmer |
| 7,151,374 B2 | 12/2006 | Doty |
| 7,160,291 B2 | 1/2007 | Damasco |
| 7,160,292 B2 | 1/2007 | Moorman |
| 7,165,422 B2 | 1/2007 | Little |
| 7,189,228 B2 | 3/2007 | Eum |
| 7,204,833 B1 * | 4/2007 | Osorio et al. .................. 606/22 |
| 7,207,985 B2 | 4/2007 | Duong |
| 7,213,400 B2 | 5/2007 | Dickerson |
| 7,220,257 B1 * | 5/2007 | Lafontaine .................. 606/21 |
| 7,223,080 B2 | 5/2007 | Duron |
| 7,250,046 B1 | 7/2007 | Fallat |
| 7,252,648 B2 | 8/2007 | Honda |
| 7,255,693 B1 | 8/2007 | Johnston |
| 7,273,479 B2 | 9/2007 | Littrup |
| 7,278,991 B2 | 10/2007 | Morris |
| 7,280,623 B2 | 10/2007 | Gupta |
| 7,282,919 B2 | 10/2007 | Doty |
| 7,288,089 B2 | 10/2007 | Yon |
| 7,318,327 B2 | 1/2008 | Dickerson |
| 7,344,530 B2 | 3/2008 | Bischof |
| 7,344,531 B2 | 3/2008 | Bischoff |
| 7,354,434 B2 | 4/2008 | Zvuloni |
| 7,361,187 B2 | 4/2008 | Duong |
| 7,381,207 B2 | 6/2008 | Duong |
| 7,458,968 B2 | 12/2008 | Carroll |
| 7,485,117 B2 | 2/2009 | Damasco |
| 7,498,812 B2 | 3/2009 | Doty |
| 7,510,554 B2 | 3/2009 | Duong |
| 7,563,260 B2 | 7/2009 | Whitmore |
| 2001/0047129 A1 | 11/2001 | Hall |
| 2002/0016540 A1 | 2/2002 | Mikus |
| 2002/0022832 A1 | 2/2002 | Mikus |
| 2002/0040220 A1 | 4/2002 | Zvuloni |
| 2002/0077654 A1 | 6/2002 | Javier |
| 2002/0085921 A1 | 7/2002 | Gram |
| 2002/0144509 A1 | 10/2002 | Chalk |
| 2002/0156469 A1 | 10/2002 | Yon |
| 2002/0157402 A1 | 10/2002 | Drube |
| 2002/0160640 A1 | 10/2002 | Korpan |
| 2002/0161385 A1 | 10/2002 | Wiener |
| 2003/0060762 A1 | 3/2003 | Zvuloni |
| 2003/0079480 A1 | 5/2003 | Emmer |
| 2003/0126867 A1 | 7/2003 | Drube |
| 2003/0135119 A1 | 7/2003 | Lee |
| 2003/0181897 A1 | 9/2003 | Thomas |
| 2003/0220635 A1 | 11/2003 | Knowlton |
| 2004/0024391 A1 | 2/2004 | Cytron |
| 2004/0055316 A1 | 3/2004 | Emmer |
| 2004/0078033 A1 | 4/2004 | Levin |
| 2004/0215178 A1 | 10/2004 | Maurice |
| 2005/0016185 A1 | 1/2005 | Emmer |
| 2005/0038422 A1 | 2/2005 | Maurice |
| 2005/0056027 A1 | 3/2005 | White |
| 2005/0086949 A1 | 4/2005 | Noble |
| 2005/0106153 A1 | 5/2005 | Nordouist |
| 2005/0177147 A1 | 8/2005 | Vancelette |
| 2005/0192564 A1 | 9/2005 | Cosman |
| 2005/0214268 A1 | 9/2005 | Cavanagh |
| 2005/0274142 A1 | 12/2005 | Corey |
| 2006/0049274 A1 | 3/2006 | Hume |
| 2006/0053165 A1 | 3/2006 | Hume |
| 2006/0079867 A1 | 4/2006 | Berzak |
| 2006/0122590 A1 | 6/2006 | Bliweis |
| 2006/0155267 A1 | 7/2006 | Berzak |
| 2006/0155268 A1 | 7/2006 | Amir |
| 2006/0264920 A1 | 11/2006 | Duong |
| 2006/0293647 A1 | 12/2006 | McRae |
| 2007/0000259 A1 | 1/2007 | Brook |
| 2007/0093710 A1 | 4/2007 | Maschke |
| 2007/0129626 A1 | 6/2007 | Mahesh |
| 2007/0129629 A1 | 6/2007 | Beauregard |
| 2007/0149959 A1 | 6/2007 | DeLonzor |
| 2007/0166171 A1 | 7/2007 | Kondo |
| 2007/0167939 A1 | 7/2007 | Duong |
| 2007/0276360 A1 | 11/2007 | Johnston |
| 2008/0027419 A1 | 1/2008 | Hamel |
| 2008/0051774 A1 | 2/2008 | Ofir |
| 2008/0051776 A1 | 2/2008 | Bliweis |
| 2008/0115509 A1 | 5/2008 | Gullickson |
| 2008/0119834 A1 | 5/2008 | Vancelette |
| 2008/0119838 A1 | 5/2008 | Vancelette |
| 2008/0319433 A1 | 12/2008 | Geiselhart |
| 2009/0011032 A1 | 1/2009 | LePivert |

FOREIGN PATENT DOCUMENTS

| | | |
|---|---|---|
| DE | 202004008875 | 8/2004 |
| DE | 102005050344 | 5/2007 |
| EP | 0292922 | 11/1988 |
| EP | 395307 | 10/1990 |
| EP | 570301 | 11/1993 |
| EP | 955012 | 11/1999 |
| EP | 919197 | 2/2005 |
| GB | 1108905 | 4/1968 |
| GB | 1108905 A | 4/1968 |
| GB | 1402737 | 8/1975 |
| GB | 1473856 | 5/1977 |
| GB | 1534472 | 12/1978 |
| GB | 2336781 | 11/1999 |
| GB | 2336781 A | 11/1999 |
| GB | 2409815 | 7/2005 |
| JP | 2004041428 | 2/2004 |
| JP | 2007144180 | 6/2007 |
| JP | 2007167100 | 7/2007 |
| WO | WO8303961 | 11/1983 |
| WO | WO9637158 | 11/1996 |
| WO | WO9639960 | 12/1996 |
| WO | WO9947876 | 9/1999 |
| WO | WO0137919 | 5/2001 |
| WO | WO0141683 | 6/2001 |
| WO | WO0197702 | 12/2001 |
| WO | WO0202026 | 1/2002 |
| WO | WO03015651 | 2/2003 |
| WO | WO2004060465 | 7/2004 |
| WO | WO2004051409 | 8/2004 |
| WO | WO2004089183 | 10/2004 |
| WO | WO2004093635 | 11/2004 |
| WO | 20050000106 A | 1/2005 |
| WO | WO2005098308 | 10/2005 |
| WO | WO2005000106 | 12/2005 |
| WO | WO2006116457 | 11/2006 |
| WO | WO2006127467 | 11/2006 |
| WO | WO2007028232 | 3/2007 |
| WO | WO2007086056 | 8/2007 |
| WO | WO2007129308 | 11/2007 |

OTHER PUBLICATIONS

International search report and written opinion for PCT/IL2008/000794, Nov. 5, 2008.

International search report and written opinion for PCT/IB2009/052615, Dec. 23, 2009.

International search report and written opinion for PCT/IB2009/000062, Jul. 23, 2009.

International search report and written opinion for PCT/IL2008/001114, Dec. 22, 2008.

International search report and written opinion for PCT/IB2009/051532, Sep. 4, 2009.
International search report and written opinion for PCT/IL2008/000943, Nov. 28, 2008.
International search report and written opinion for PCT/IL2007/001103, Sep. 6, 2007.
International search report and written opinion for PCT/IL2007/001142, Sep. 18, 2007.
International search report and written opinion for PCT/IL2007/000974, Aug. 5, 2007.
S L Qi et al, "Flow boiling of liquid nitrogen in micro-tubes: Part I—onset of nucleate boiling, two phase flow instability and two phase flow drop", International Journal of Heat and Mass Transfer, vol. 50, 2007, pp. 4999-5016.
S L Qi et al, "Flow boiling of liquid nitrogen in micro-tubes: Part II—heat transfer characteristics and critical heat flux", International Journal of Heat and Mass Transfer, vol. 50, 2007, pp. 5017-5030.
P Zhang et al, "Two phase flow characteristics of liquid nitrogen in vertically upward 0.5 and 1.0 mm micro-tubes: Visualization studies", Cryogenics, vol. 49, 2009, pp. 565-575.
International search report and written opinion for PCT/US2010/34467, Aug. 24, 2010.
International Search Report for PCT/IB2009/051532, dated Aug. 26, 2009.
S.L. Qi et al. "Development and Performance Test of a Cryoprobe With Heat Transfer Enhancement Configuration" Cryogenics 46(2006) 881-887.

* cited by examiner

CRYOSURGICAL INSTRUMENT WITH ENHANCED HEAT EXCHANGE

CROSS REFERENCE TO RELATED APPLICATIONS

This application is a national stage filing under section 371 of International Application No. PCT/IB2009/051532, filed on Apr. 13, 2009, and published in English on Oct. 22, 2009, as WO 2009/0128014 and claims priority of U.S. application No. 61/045,372 filed on Apr. 16, 2008, the entire disclosure of these applications being hereby incorporated herein by reference.

FIELD OF THE INVENTION

The present invention relates to cryosurgical equipment, and, in particular, to cryoprobes intended to be inserted in tissue or to be brought in contact with the tissue in order to perform a cryosurgical procedure.

BACKGROUND OF THE INVENTION

Cryoprobes are known in the art for inducing a lower temperature or freezing in tissues. Typically, a cryogen is delivered into a cryoprobe in the form of mist, i.e., in the form of small cryogen droplets distributed in the vapors of the cryogen itself. A certain fraction of the liquid cryogen evaporates during delivery to the cryoprobe as a result of imperfections in the thermal insulation of a delivery hose. The cryogen mist cannot be separated completely in the internal cavity of the cryotip (the distal section of the cryoprobe) on the liquid and gaseous phases without application of special measures. Without such special means, it is impossible to use completely the liquid fraction of the cryogen for effective freezing.

There were some previous attempts with limited success to solve this problem. U.S. Pat. No. 5,324,286 describes a cryogenic apparatus which comprises a coolant system and a probe having a cryogenically-cooled tip. The probe is formed of an elongated housing having a distal end closed by the tip and a proximal end connected to the coolant system. The housing is adapted to receive cryogenic droplets entrained in a warm carrier gas stream supplied by the coolant system. The carrier gas stream passes through the housing such that the entrained cryogenic droplets are transported to the distal end of the probe for cooling the cold-tip. The tip is cryogenically-cooled by the cryogenic droplets which are collected at the base of the tip. More specifically, the carrier gas transports the entrained cryogenic droplets, through the inlet tube to the distal end of the probe where, because of their inertia, the droplets cannot follow the 180 degree bend of the returning carrier gas stream. Instead, the droplets are deposited and stored in a porous heat sink positioned in the cold-tip. The porous heat sink is positioned such that it is in thermal contact with a cold-tip head. Both the porous heat sink and the tip head are formed of a thermally conductive material. The liquid deposited in the heat sink from impinging droplets is evaporated by heat supplied by the object to be cooled, such as tumor tissue which is placed in contact with the cold-tip head. Accordingly, the tip reaches temperatures commensurate with the saturation temperature of the evaporating liquid cryogen.

U.S. Pat. No. 5,264,116 describes a cryoprobe with separation means in the form of a liquid nitrogen supply tube, which is provided with a plurality of small vent holes to vent gas formed or present in the refrigerant supply tube to the return refrigerant flow channel. The vent holes also allow a small amount of liquid nitrogen to vent into the return flow channel to further reduce the temperature differential between the sub-cooled liquid nitrogen supply and the counter-current flowing return refrigerant.

An analagous technical solution is described in U.S. Pat. No. 5,520,682. However, such design of a separator cannot ensure effective separation of liquid and gaseous phases of the cryogen mixture.

An article by S. L. Qi et al. "DEVELOPMENT AND PERFORMANCE TEST OF A CRYOPROBE WITH HEAT TRANSFER ENHANCEMENT CONFIGURATION" CRYOGENICS 46 (2006) 881-887, describes a cryosurgical system, which functions on the basis of liquid nitrogen, supplied into a cryoprobe from a dewar flask. In order to improve quality of the liquid-gaseous mixture supplied from the dewar flask, there is a separator, which is positioned immediately after the dewar flask and serves for separation between the liquid and gaseous phases of the stream.

However, this technical solution cannot provide complete separation of gaseous and liquid phases because of the process of further gasification of the liquid nitrogen, which occurs in the supplying hose of the system and in the cryoprobe itself as a result of imperfection of their thermal insulations.

U.S. Pat. Nos. 4,831,856 and 5,800,487, among others, describe application of helical tubes as counter-flow heat exchangers in cryosurgical instruments operating on the principle of Joule-Thomson.

SUMMARY OF THE INVENTION

The background art does not teach or suggest a cryoprobe which provides efficient heat transfer at the distal end of the probe. The background art also does not teach or suggest the use of helical tubes for droplet separators and/or internal fins as described herein.

The present invention provides a cryosurgical instrument that features a cryogen in liquid or liquid-gaseous (mist) form being supplied into the internal space of the distal section of the cryosurgical instrument, which is terminated by a cryotip. Fins of a special form are provided in order to separate droplets.

The cryosurgical instrument of the present invention comprises a shaft, which ends at its distal edge with a cryotip.

A feeding lumen is situated in the shaft and sealed with its proximal edge. The proximal end of the feeding lumen protrudes from the proximal end of the shaft and is terminated with a connection inlet serving for supply of the liquid or gaseous cryogen into the internal space of the cryotip. The proximal section of the shaft is provided with an outlet connection with a function to remove the evaporated cryogen from the internal space of the cryosurgical instrument.

In addition, the shaft is provided with a layer of thermal insulation intended to minimize or prevent any undesired freezing effect of the cryogen on surrounding tissue.

In order to achieve high values of heat transfer from the internal wall of the cryotip to the supplied cryogen, the distal section of the feeding lumen preferably has a form of a helical tube, which is situated in tight thermal contact with the internal wall of the cryotip. The distal end of this helical tube is open, so that the cryogen enters from this distal end into the internal space of the cryotip and then is exhausted via the outlet connection of the cryosurgical instrument.

The helical tube preferably provides internal fins for the envelope of the cryotip. Such an exemplary form of the internal fins has a significant advantage: in the process of the cryogen flowing in the helical section of the feeding lumen, heat transfer coefficient of the cryogen to the internal wall of this helical section achieves very high value.

Without wishing to be limited by a single hypothesis, it is believed that this enhancement of heat transfer is based on two physical phenomenon: eddying flow separation of the droplets in the distal helical section of the feeding lumen and higher value of heat transfer coefficient of the gaseous fraction of the cryogen to the internal wall of the helical tube because of its eddying motion and the decreased hydraulic diameter of the feeding lumen in the helical portion.

There are some optional embodiments to ensure good thermal contact between the helical section of the feeding lumen and the internal wall of the envelope of the cryotip.

In an embodiment of the present invention, there is mechanical contact between the helical tube and the internal surface of the cryotip envelope. This contact can be improved by abrading the outer surface (to be in the contact with the internal wall of the cryotip envelope) of the helical tube.

In another embodiment of the invention, the helical tube is soldered or otherwise joined directly to the internal surface of the cryotip envelope.

In yet another embodiment of the invention, the helical tube and the internal surface of the cryotip envelope are optionally and preferably joined by deposition of chemical nickel, copper or silver, or any other suitable material, as it is known in the art of electroplating.

It should be noted that the helical tube preferably has a pitch that provides an eddying flow of the cryogen outside to the helical tube, which provides an additional effect of eddying flow separation for the cryogen flowing in the internal space of the cryotip envelope outside to the helical section of the feeding lumen.

In some embodiments, the heat transfer coefficient for the cryogen flowing in the helical section of the feeding lumen is enhanced by inserting a metal wire spiral into the distal section of the feeding lumen before winding this distal section in the form of the helical tube. The outer diameter of the metal wire spiral fits the internal diameter of the feeding lumen, such that this metal wire spiral provides an internal fin of the distal section of the feeding lumen, which, after winding this distal section provides an additional factor of heat transfer enhancement for the internal surface of the helical distal section of the feeding lumen.

The above embodiments support the important function of separating liquid droplets of the cryogen and its gaseous phase immediately near the internal surface of the cryotip and directing the obtained liquid phase on the internal surface following boiling and evaporation of this liquid phase.

DESCRIPTION OF PREFERRED EMBODIMENTS

Figure 1A:
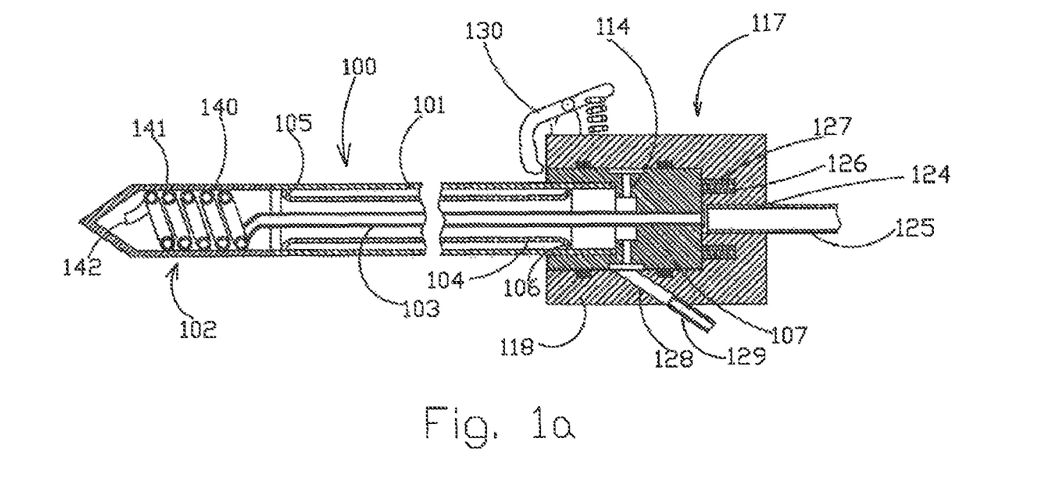
FIG. 1a is an axial cross-section of a cryosurgical instrument with application of a bushing as a joining element of the cryoprobe construction and a female unit of the quick coupling.

FIG. 1a is an axial cross-section of a cryosurgical instrument with application of a bushing as a joining element of the cryoprobe construction and a female unit of the quick coupling.

Figure 1B:
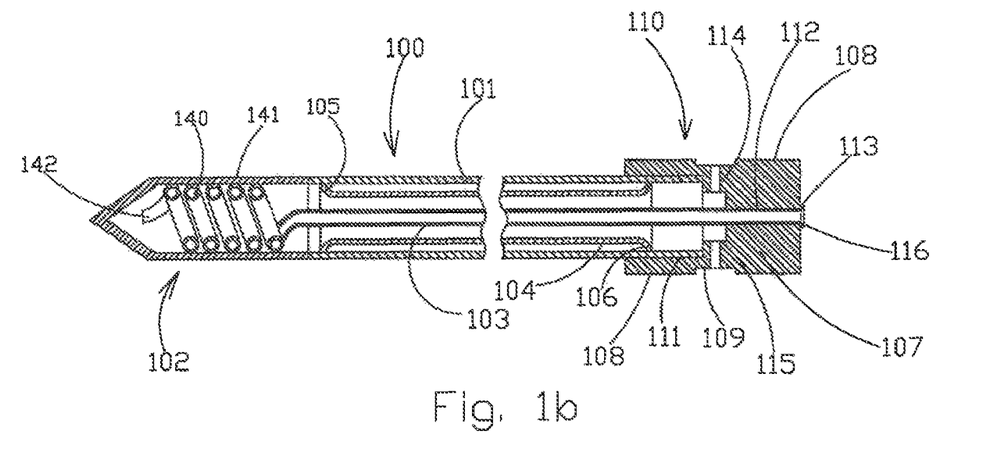
FIG. 1b is an axial cross-section of a cryosurgical instrument with application of a bushing as a joining element of the cryoprobe construction.

FIG. 1b is an exploded axial cross-section of a cryotip of the cryosurgical instrument with a distal section of a feeding lumen in the form of a helical tube.

This embodiment of cryoprobe 100 comprises shaft 101, which terminates at its distal edge with cryotip 102. Shaft 101 is preferably fabricated from a rigid material in the case of the design of the cryosurgical instrument as a cryoprobe, and from a flexible material in the case of the design of the cryosurgical instrument as a cryocatheter.

A feeding lumen 103 is situated in shaft 101; the proximal end of the feeding lumen 103 preferably protrudes from the proximal end of shaft 101. The extreme proximal section of the feeding lumen 103 is preferably longitudinally turned. The proximal sections of shaft 101 and the feeding lumen 103 receive a male unit 110 which together comprise a quick coupling mechanism.

Figure 1C:
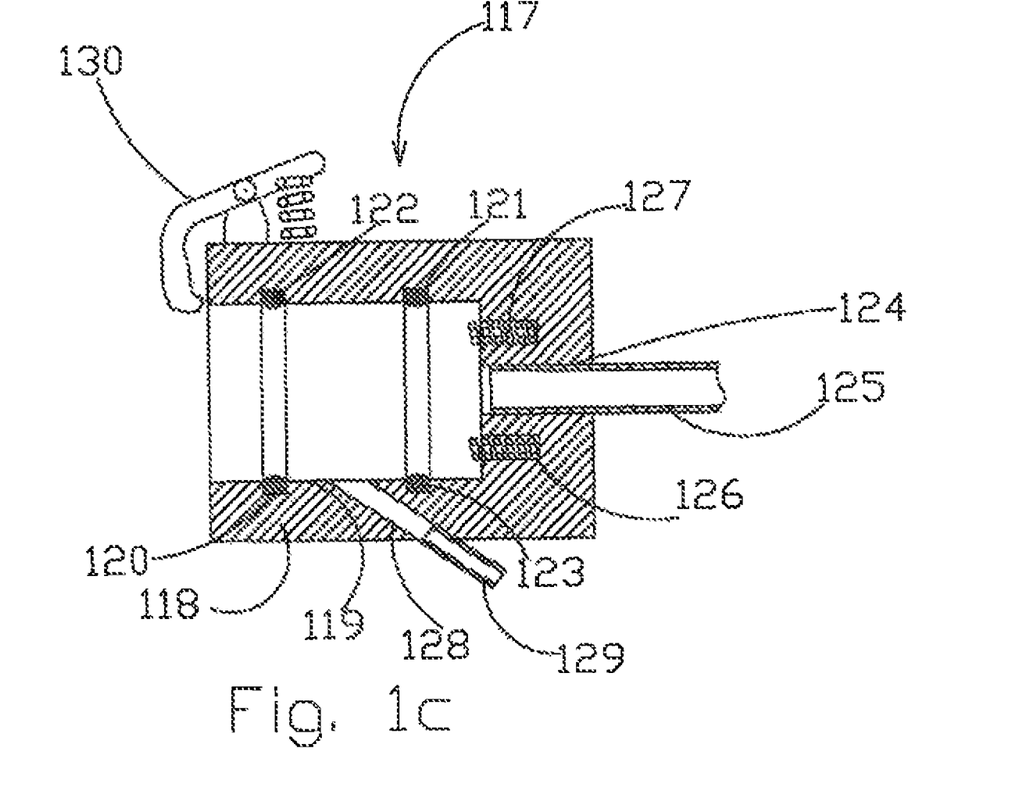
FIG. 1c is an axial cross-section of the female unit of the quick coupling.
Figure 1D:
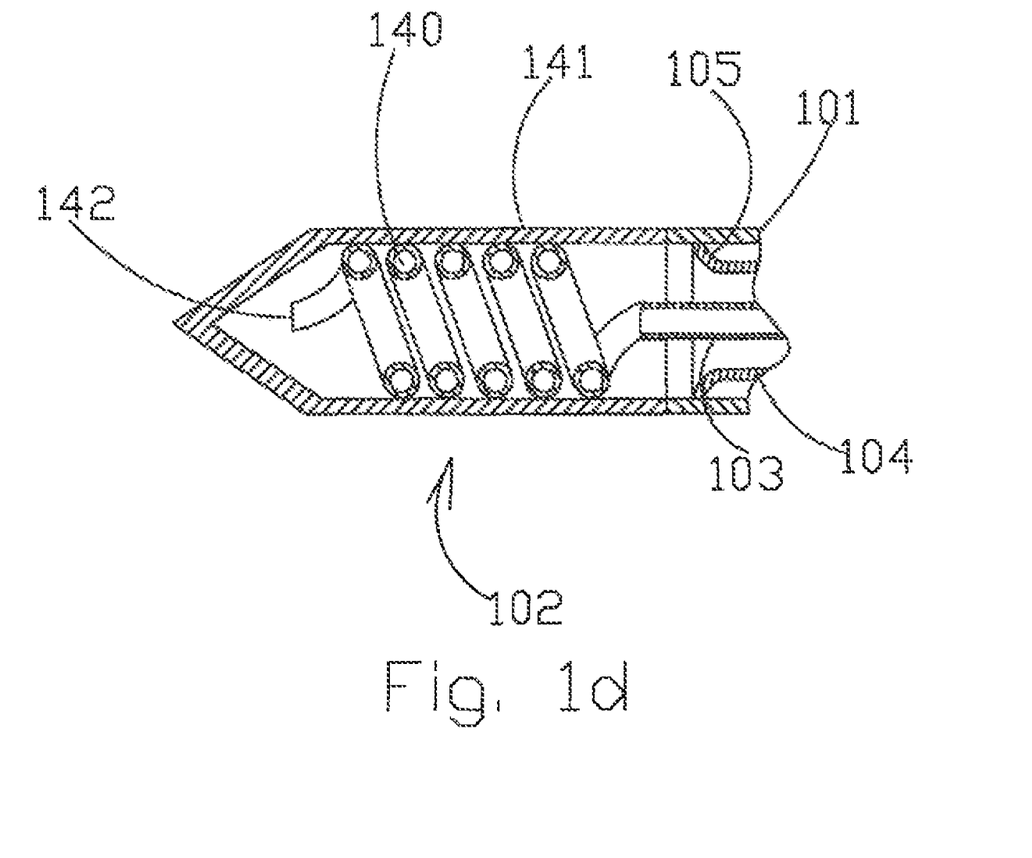
FIG. 1d is an exploded axial cross-section of a cryotip of the cryosurgical instrument with a distal section of a feeding lumen in the form of a helical tube.

The distal section 140 of the feeding lumen 103 is twisted into a helical coil, described herein as being helically coiled and is also described herein as a helical tube, so that the outer diameter of the helical coil of distal section 140 fits the inner diameter of a cylindrical envelope 141 of cryotip 102. The pitch of the helical coil into which distal section 140 is formed preferably provides an eddying flow of the cryogen around distal section 140, which provides an additional effect of eddying flow separation for the cryogen flowing in the internal space of the feeding lumen 103, after emerging from a distal end 142 of distal section 140, which is open. By "eddying flow" it is meant that various eddies are created as the cryogen flows around distal section 140, as the cryogen swirls, thereby creating turbulence.

In an embodiment of the present invention, there is mechanical contact between the helical tube of distal section 140 and the internal surface of the cryotip envelope 141. This contact can be improved by abrading the outer surface (to be in the contact with the internal wall of the cryotip envelope 141) of the helical tube.

In another embodiment of the invention, the helical tube of distal section 140 is soldered or otherwise joined directly to the internal surface of the cryotip envelope 141.

In yet another embodiment of the invention, the helical tube of distal section 140 and the internal surface of the cryotip envelope 141 are optionally and preferably joined by deposition of chemical nickel, copper or silver, or any other suitable material, as it is known in the art of electroplating.

Figure 1E:
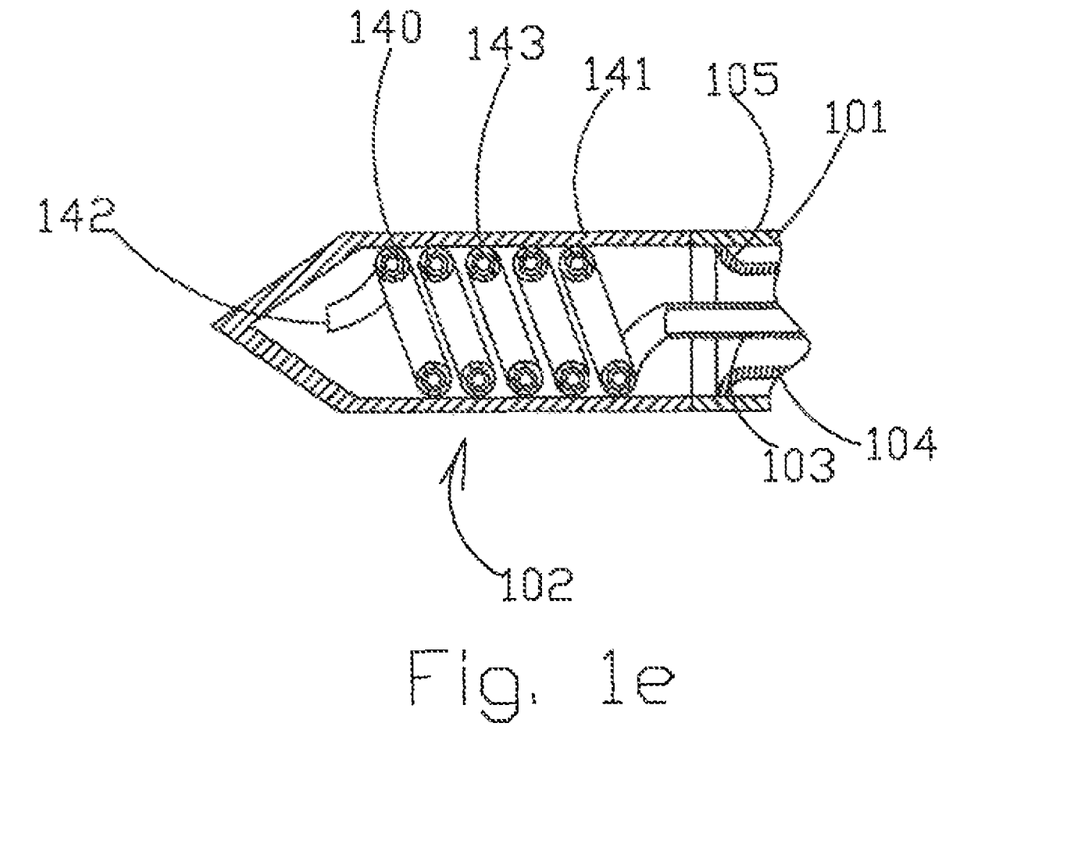
FIG. 1e is an exploded axial cross-section of a cryotip of the cryosurgical instrument with a distal section of a feeding lumen in the form of a helical tube and a wire metal spiral installed in the helical tube.

A wire spiral 143 is installed in the distal section 140 in the version shown in FIG. 1e. Wire spiral 143 may optionally and preferably be comprised of metal or any temperature conducting material. Although shown herein as a wire, wire spiral 143 may optionally be configured as any type of helical shape.

Thermal insulation of shaft 101 is provided by an intermediate tube 104 with two flanged ends 105 and 106, wherein the outer diameter of the formed flange ends 105 and 106 conforms to the internal diameter of the shaft. Friction between the internal surface of shaft 101 and flanged ends 105 and 106 ensures stable positioning of the intermediate tube 104 with regard to shaft 101.

The male unit 110 of the quick coupling, which is installed on the proximal sections of shaft 101 and the feeding lumen 103, comprises bushing 107.

The outer surface of bushing 107 comprises proximal and distal cylindrical sections 108 and a middle section 109; the proximal and distal sections 108 have the same diameter, and diameter of the middle section 109 is preferably somewhat smaller.

The inner surface of bushing 107 is preferably also stepped, such that distal, intermediate and proximal sections 111, 115 and 112 respectively of bushing 107 have progressively decreasing diameters.

Bushing 107 is installed on the proximal sections of shaft 101 and the feeding lumen 103 in such a manner that the distal section of the inner surface of the bushing is fitted tightly on the proximal section of the shaft and the proximal inner surface 112 of bushing 107 is fitted slidingly on the longitudinally turned proximal section of the feeding lumen 103. After positioning bushing 107 on the proximal section of shaft 101, the proximal edge of the feeding lumen 103 is flanged with formation flange 113 and application of a deformable o-ring 116 from a cryogenically stable polymer for sealing the gap between the proximal sections of the internal surface of bushing 107 and the feeding lumen 103. A first through channel 114 communicates the internal and external spaces of bushing 107 in the place of its inner intermediate section 115 and its outer middle section 109.

A female unit 117 of the quick coupling mechanism is designed as housing 118, with a cylindrical inner cavity, wherein the diameter of the cylindrical section 119 of the inner cavity conforms to the outer diameter of the distal and proximal sections 108 of bushing 107.

The cylindrical section 119 is provided with distal and proximal annular grooves 120 and 121, which serve for installation of steady sealing O-rings 123 and 122.

A through opening 124 in the proximal face plane of the inner cavity serves for installation of an inlet connection 125 supplying the cryogen into cryoprobe 100. It should be noted that the tolerances of the bushing 107 and the housing 118 permit sliding insertion of bushing 107 of cryoprobe 100 into housing 118 of the female unit 117; the polymer o-rings 123 and 122 installed in the aforementioned annular grooves 120 and 121 of housing 118 provide sealing.

In addition, the inner surface of the face plane of housing 118 is provided with blind holes 126 and helical springs 127, which are partially situated in these blind holes 126. In the process of coupling, the male unit 110 of the coupling pair is spring-actuated by these helical springs 127.

A second through channel 128 with an outlet connection 129 installed on the outer end of the second through channel 128 communicates the annular channel formed between the middle section 109 of bushing 107 and the outside space of housing 118.

First through channel 114, the formed annular channel and second through channel 128 serve for exhausting evaporated cryogen from cryoprobe 100.

The heat transfer coefficient for the cryogen flowing through distal section 140 of the feeding lumen 103 is preferably enhanced by inserting wire spiral 143, which as noted above preferably comprises metal or any temperature conductive material, into the distal section 140 of the feeding lumen 103, before distal section 140 assumes its helical form. The outer diameter of the wire spiral 143 fits the internal diameter of the feeding lumen 103, such that wire spiral 143 provides an internal fin of the distal section 140 of the feeding lumen 103. This arrangement provides an additional factor of heat transfer enhancement for the internal surface of the helical distal section 140 of the feeding lumen 103.

Persons skilled in the art will appreciate that the present invention is not limited to what has been particularly shown and described hereinabove. Rather the scope of the present invention is defined by the appended claims and includes both combinations and sub combinations of the various features described hereinabove as well as variations and modifications thereof, which would occur to persons skilled in the art upon reading the foregoing description.

The invention claimed is:

1. A cryosurgical instrument operating on cryogen in liquid or gaseous-liquid forms; comprising:
    an external shaft;
    a cryotip joined with a distal edge of said external shaft;
    a feeding lumen, at least partially situated in an internal space of said external shaft and cryotip, wherein a proximal edge of said external shaft is joined with a proximal section of said feeding lumen; and
    wherein a distal section of said feeding lumen is helically coiled, so that an outer diameter of the helically coiled distal section fits an inner diameter of a cylindrical envelope of said cryotip, and said helically coiled distal section and said cylindrical envelope are in thermal contact, the instrument further comprising a wire spiral installed in the helically coiled distal section.

2. The instrument of claim 1, wherein the thermal contact between the cylindrical envelope and the helically coiled distal section is provided mechanically by physical contact between the cylindrical envelope and the helically coiled distal section.

3. The instrument of claim 1, wherein the thermal contact between the cylindrical envelope and the helically coiled distal section is provided by solder joining the cylindrical envelope and the helically coiled distal section together.

4. The instrument of claim 1, wherein the thermal contact between the cylindrical envelope and the helically coiled distal section is provided by a chemical deposition of a metal coating.

5. The instrument of claim 1, wherein said wire spiral comprises a metal.

6. The instrument of claim 1, further comprising a proximal coupling unit, which includes an inlet connection for delivery of said cryogen into said feeding lumen and an outlet connection for removal of a gaseous component of said cryogen; and a thermal insulation unit of said external shaft.

\* \* \* \* \*